United States Patent [19]

Eaton et al.

[11] Patent Number: 5,234,006

[45] Date of Patent: Aug. 10, 1993

[54] ADJUSTABLE SUTURES AND METHOD OF USING THE SAME

[76] Inventors: Alexander M. Eaton, 910 Constitution Ave., Durham, N.C. 27715; Cemil M. Purut, 500 N. Duke St., Apt. 53-202, Durham, N.C. 27701

[21] Appl. No.: 642,816

[22] Filed: Jan. 18, 1991

[51] Int. Cl.⁵ ............................................. A61B 19/00
[52] U.S. Cl. ..................................... 128/898; 606/228
[58] Field of Search ..................... 606/228–231, 606/78; 428/913, 34.9; 524/88; 128/898

[56] References Cited

U.S. PATENT DOCUMENTS

| | | | |
|---|---|---|---|
| 3,386,841 | 6/1968 | Braun | 524/88 |
| 3,513,848 | 5/1970 | Winston et al. | 606/228 |
| 3,620,218 | 11/1971 | Schmitt | 128/334 |
| 3,630,205 | 12/1971 | Listner . | |
| 3,707,972 | 1/1973 | Villari et al. | 128/349 |
| 3,783,454 | 1/1974 | Sausse et al. | 128/334 |
| 3,786,806 | 1/1974 | Johnson et al. . | |
| 3,818,511 | 6/1974 | Goldberg et al. | 128/214 |
| 3,818,515 | 6/1974 | Neville | 128/334 |
| 3,833,940 | 9/1974 | Hartenbach | 128/334 |
| 3,918,455 | 11/1975 | Coplan | 606/225 |
| 3,943,933 | 3/1976 | Gertzman | 606/227 |
| 3,981,307 | 9/1976 | Borysko | 606/227 |
| 4,024,871 | 5/1977 | Stephenson | 606/231 |
| 4,265,235 | 5/1981 | Fukunaga | 128/200.24 |
| 4,365,031 | 12/1982 | Massey et al. | 524/88 |
| 4,470,415 | 9/1984 | Wozniak . | |
| 4,485,816 | 12/1984 | Krumme . | |
| 4,537,183 | 8/1985 | Fogarty | 128/79 |
| 4,596,728 | 1/1986 | Yang et al. . | |
| 4,820,755 | 4/1989 | Webster | 524/88 |
| 5,002,563 | 3/1991 | Rika et al. | 606/222 |
| 5,049,600 | 9/1991 | Kletecka | 524/88 |
| 5,084,063 | 1/1992 | Korthoff | 606/228 |

OTHER PUBLICATIONS

Encyclopedia of Polymer Science & Technology, vol. 11, pp. 339–373 (1969).

*Primary Examiner*—Stephen C. Pellegrino
*Assistant Examiner*—Gary Jackson
*Attorney, Agent, or Firm*—Hopgood, Calimafde, Kalil, Blaustein & Judlowe

[57] ABSTRACT

A method of suturing using a suture made from materials which, upon application of energy, contract or expand after implantation in tissues and/or prosthetic materials same.

7 Claims, No Drawings

ADJUSTABLE SUTURES AND METHOD OF USING THE SAME

FIELD OF THE INVENTION

The present invention relates generally to sutures used to repair tissues whose dimensions may be modified in vivo, a method of repairing tissues using the sutures, and particularly to sutures whose axial dimension and cross-sectional area may be altered after implantation in the tissue or prosthetic material.

BACKGROUND OF THE INVENTION

Surgical sutures are generally categorized as absorbable or non-absorbable depending upon whether the suture material is degraded and absorbed by the body. Both categories of sutures are made from natural or synthetic materials. Sutures are further differentiated based on whether the suture is made of a single filament (monofilament) or multiple filaments that are twisted or braided. All sutures may be provided with variety of coatings which serve to both minimize friction as the suture is passed through the tissue and to decrease tissue reactivity.

The choice of suture for a given surgical procedure is based on the properties of the suture material and the response of the tissue being repaired. However, all suture materials are at least required to be strong enough to carry the applied load, and to substantially maintain dimensional integrity after implantation.

It is well recognized that the natural response of tissue to injury, even injury resulting from a careful and appropriate surgical technique, is one of extracellular fluid accumulation (edema) in the vicinity of the wound. Thus, sutures which have been appropriately placed and tensioned at the time of surgery may operate to excessively constrict the tissue as edema forms post-operatively. Excessive constriction results in strangulation and necrosis of the tissue.

It is often difficult to anticipate at the time of surgery how much edema will form post-operatively. Thus, it is not feasible to leave sutures slack at the time of placement in the hope that subsequent edema will ensure an appropriate suture tension. Moreover, poor initial approximation resulting from the placement of a slack suture can allow entry of bacteria and contribute to wound dehiscence.

Sutures are sometimes placed in previously inflamed tissue which is edematous at the time of the surgical repair, as a result of (1) tissue inflammation and/or (2) an injection of an anesthetic and/or hemostatic agent into the wound margins. In this circumstance, the sutures are tensioned to accommodate the edematous tissue. In the immediate post-operative period, the sutures may slacken as the edema resolves. This can result in bacteria entering the wound and poor wound healing.

Proper suturing requires that the sutures be tensioned just enough to approximate, but not strangulate, the tissue. For example, in skin closure, small bites of tissue with the needle placed at 2 to 3 mm from the skin edges keeps the amount of tissue under tension relatively small, and helps to minimize scarring. Wound edema in the early post-operative period increases the tension on the skin between sutures. This frequently results in permanent skin suture marks, especially if the sutures are allowed to remain for prolonged periods. (S. J. Aston; "The Choice of Suture Material for Skin Closure". *J. of Derm. Surg.* 2(1): 57–61, March 1976), incorporated herein by reference.

Proper tensioning of sutures even in the hands of a skilled surgeon is difficult, subject to error, and time consuming. When a suture is tensioned too tightly, or becomes too tight as a result of tissue edema, the surgeon must cut the suture using a scalpel, scissors or laser. (Marc F. Liebermanx, "Suture Lysis by Laser and Goniolens" *Am. J. Ophth.* 95(2): 257–258, 1983). However, removal of a tight suture can result in gaping of the wound and subsequent scarring. Furthermore, additional time is needed to correct the problem thereby further extending the surgical procedure.

When a suture is tensioned too loosely, or there is loosening of the suture post-operatively, the suture must be replaced. This is time consuming as is the case with overly tight sutures, and in some instances may require a return to the operating room. Moreover, although intended to improve wound apposition and reduce scar formation, the replacement of sutures further traumatizes the tissues they are meant to repair.

Previous attempts at overcoming the difficulties with suture tension have included the replacement of sutures with a heat-shrinkable sleeve for vessel anastomosis. John J. Wozniak, U.S. Pat. No. 4,470,415 discloses the placement of a heat-shrinkable sleeve around the vessels to be joined and heating them with a wand or other suitable heat transmitting applicator. These heat-shrinkable sleeves suffer from a number of disadvantages. First, their use is limited to tubular members, and is of little value in other anastomoses, such as skin and cataract incision closure. Second, their placement requires the use of two ferrules, which become permanently incorporated into the wound. These ferrules can be made of degradable materials or non-degradable materials. The degradable materials mentioned, such as collagen and polyglycolate, cause an inflammatory response, which may lead to thrombosis and vascular occlusion. The non-degradable materials, such as polyethylene, can lead to foreign body reactions, or can erode into the vessels they are meant to repair, resulting in wound failure, infection, or thrombosis.

John F. Krumme, U.S. Pat. No. 4,485,816 discloses another approach to the eliminating of problems associated with suture repair. Staples made from a material having the intrinsic property of shape memory (e.g. nickel-titanium alloys) are used in place of sutures. The staples are formed at low temperatures in a shape which expedites entry into the tissue and then deformed into a tissue-gripping shape upon subsequent heating. Such staples are disadvantageous because, like conventional suture techniques, once inserted and deformed into a tissue-gripping shape, the tension of the staples cannot be adjusted.

Because of the difficulties in obtaining proper suture tension both intra-operatively and post-operatively using conventional sutures and alternatives including, staples and heat shrinkable sleeves as described above, there remains a need for the development of an easy to use suture whose dimensions, particularly the linear dimension can be altered after implantation in the tissue or prosthetic material.

It is therefore an object of the present invention to provide a suture whose dimensions can be altered after implantation to relieve or increase tension on the tissue or prosthetic material.

It is another object of the present invention to increase or decrease the cross-sectional area of the suture to prevent leakage around the insertion site in the anastomoses of fluid containing structures such as blood vessels, bowel and meninges.

It is a further object of the invention to provide a suture whose dimensions can be altered by the application of energy without damaging the tissue.

It is a further object of the invention to provide a method of suturing tissues or prosthetic materials employing a suture whose dimensions can be altered after implantation either at the time of surgery or in the post-operative period.

SUMMARY OF THE INVENTION

The present invention is directed to sutures which are suitable for reapproximation of divided biologic tissues and prosthetic materials, and for the ligation of vascular and other tubular structures. The dimensions of the sutures can be adjusted after implantation to provide proper tension and/or to prevent leakage around the insertion site in the anastomoses of fluid containing structures such as blood vessels, bowel and meninges.

The sutures in accordance with the present invention can expand or contact so that the size of the suture may be adjusted for a particular application. This allows for greater control of tissue reapproximation, thereby reducing tissue trauma, and reducing post-operative scar formation. The expansion or contraction of the suture material of the present invention occurs along two axes. When the axial length of the suture is increased its cross-sectional diameter decreases, and conversely when its axial length is shortened, its cross-sectional increases. The changes in suture diameter, which occur as a result of elongation and shortening along the axial length, are useful for other applications. For example, in vascular and bowel anastomoses, there is frequently leakage of blood or intestinal fluid around the suture site which increases the length of the operation and the potential for post-operative complications such as infection or graft failure. This is particularly common in anastomosis of prosthetic graft material to native tissue. To overcome this problem, a suture material made to impart significant shrinkage upon the application of energy, such as heat, can be inserted and tied in a loose fashion. The application of heat near the insertion site, for example, using a laser, will result in the shortening and thickening of the suture. This thickened suture can then be rotated into the incision site which is leaking, thereby reducing the amount of leakage present. Moreover, the precise control of suture tension afforded by the suture material of the present invention, will insure that the material is well tensioned.

The suture of the present invention is made from any acceptable material which may be processed so that its dimensions can be altered in vivo without damaging the surrounding tissue or prosthetic material. Such sutures are preferably made from heat sensitive materials which are particularly suited for adjustment after implantation. Examples of these materials include, but are not limited to, silicone rubber, polystyrene, substituted and unsubstituted polyolefins (e.g. polyethylene, polytetrafluoroethylene and polypropylene) poly(vinylidene chloride), polyester, poly(vinyl chloride), poly(vinyl fluoride), coated cellophanes, polyvinyl acetate and poly(methyl methacrylate), and combinations thereof. Specific heat sensitive materials which are known to be biocompatible belong to the general classes of polyethylenes, polypropylenes, polyesters, poly(methylmethacrylate) and polyoxides. The preferred suture materials are polyolefins, including polypropylene and mixtures of polyolefins alone or in combination with other compatible polymers such as polyvinyl acetate.

DETAILED DESCRIPTION OF THE INVENTION

Heat-sensitive materials, which are preferred materials employed in the present invention, are widely used to package foods, and in the electronics industry to protect and encapsulate electronic components.

The ability to change dimensions, particularly to shrink upon the application of energy can be imparted to heat-sensitive materials through the use of monoaxial or biaxial stretching (*Encyclopedia of Polymer Science and Technology;* Interscience Publishers. John Wiley & Sons, Vol 11, 1969), incorporated herein by reference. The materials may be modified by copolymerization with up to 40% of one or more comonomers, including, but not limited to, polyesters, poly(vinyl fluoride), polypropylene, polyethylene, and poly(methyl methacrylate). Stretching of a material below the softening temperature orients the polymer molecules and crystallites in the direction of stretch, leading to changes in the stress-strain characteristics of the material. Both the modulus of elasticity and the ultimate strength are increased by this process, but the elongation at break and dimension stability with respect to temperature decreases. (See also, *Ullman's Encyclopedia of Industries Chemistry,* Verlaggeselischuft, 1988, incorporated herein by reference).

Procedures to orientate the fibers are dependent on the type of polymer being used. For noncrystallizable polymers, the polymer is heated to a temperature at which it becomes a viscous liquid, then is cooled homogeneously to as close to the glass-transition temperature as is practical for stretching. The material is then stretched either at a constant temperature or under a falling temperature gradient, and is subsequently quenched to below the glass-transition temperature. (*Encyclopedia of Polymer Science and Technology;* Interscience Publishers, John Wiley and Sons, Vol. 11 1969).

For crystallizable polymers, the polymer is heated to a temperature above its crystalline melting point and held there until all traces of crystallinity have disappeared. The polymer is then cooled as rapidly as possible to below the temperature of maximum crystallization rate. If feasible, the material should be cooled below its glass-transition temperature to ensure the maintenance of a low level of crystallinity. If this low temperature is impractical, the material may be cooled to a temperature at which the crystallization rate is low enough so that no appreciable amount of crystallinity will develop in the material before it is stretched.

The resulting amorphous or nearly amorphous material is then reheated to as low a temperature as practical above the glass transition temperature and stretched rapidly to prevent crystal growth. The material can then be quenched to below the glass transition temperature or to a lower temperature above the glass transition temperature to give an essentially amorphous, readily heat-shrinkable material.

The polymeric materials used in the present invention, in general, are preferably cross-linked using irradiation or chemical reagents. Irradiation is preferred, because chemical reagents tend to leave toxic residues. Crosslinkage of the polymers enables the material to be elongated or shrunk at its original melting point, without becoming a fluid. Thus, cross-linking increases the temperature at which the material becomes a fluid, while still allowing for the material to be stretched or shrunk at its original melting point. Such a procedure results in the production of excellent shrinkable or stretchable sutures.

All oriented fibers or films shrink at a temperature between their glass-transition temperatures and their melting points or softening temperatures. At temperatures above the glass-transition temperature the material shrinks, and the rate of shrinkage increases with increasing temperature until the fiber or film is heated to a sufficiently high temperature for viscous flow to compete with retraction. Above this temperature, less than the theoretical maximum amount of shrinkage take place. With crystallizable polymers, shrinkage above the glass-transition temperature can be prevented by heat treatment during which crystallization of the oriented polymer takes place.

The degree of shrinkage can be regulated by the manufacturing process. For example, if the orientation is carried out at a low temperature, using a high stretching rate and a rapid quench, nearly all of the stretch put into the fiber is recoverable upon heating. If all other conditions remain the same, but the orientation temperature is raised, less of the original stretch is recoverable. Accordingly, the sutures of the present invention can be produced with varying ranges of shrink or stretch giving the surgeon flexibility in the selection of a suture for a particular application.

When a material is heated and restrained from shrinking it looses its orientation, but not as rapidly as if free to shrink. During this orientation loss, the material exerts a pull on the restraining clamps. The magnitude of this pull is related to the original stretch conditions and gives a measure of orientation level, although it does not always correlate with the amount of shrinkage.

It is important to note that such materials can be formulated in less oriented fashion, and through the application of energy, the suture can be stretched to increase the orientation. Then by allowing the suture to cool, either by air or water bath, the suture can be maintained in an elongated condition.

Upon the application of energy, the type of change which occurs to the suture's axial length and diameter is largely controlled by two factors. These factors are the conditions present at the time of energy input, such as heating, and the process by which the suture is manufactured. In order to shorten the axial length and increase the diameter of a suture, it is important that there is little, or preferably no tension, on the suture. Both ends of the suture should be secure, as is the case when a suture is implanted into a warm blooded animal. If the ends of the suture are free, it will kink at the point of energy application, preventing controlled shrinkage, and frequently leading to suture lysis. Forceps may be inserted under the ends of the suture to keep it elevated off of the tissue, in order to reduce the amount of thermal injury to adjacent tissues. Ideally, the tissues should be approximated together in the desired fashion before energy is applied, and the excess suture should be exposed to allow energy application. Forceps may be used for this purpose. If a small energy spot is used, such as that produced by a laser, the energy is best applied in a sweeping fashion along the length of the suture. If the sweep rate employed is too slow, thinning and breakage at the point of laser energy application may occur.

The suture will contract and its cross-sectional area will enlarge in the area to which the energy is applied. The amount of axial shrinkage and cross-sectional enlargement can be precisely controlled by four factors: (1) the density of the energy employed; (2) the length of time the energy is applied; (3) the amount of slack present in the suture; and (4) the maximum amount of shrinkage obtainable for a given suture material. Typically, upon the application of energy, such as a laser, in a sweeping fashion, the suture will contract an amount equal to the amount of slack present, and will then stop. This is ideal for the adjustment of a loose suture in vivo, as it will allow for shortening of the suture until all the excess slack is removed, and will stop without the production of excess tension as can frequently occur after manual suture placement.

In order to elongate the axial length and decrease the diameter of the suture, it is important that the suture be held in a slightly taut fashion. The tensioning of the suture is best controlled using a pair of forceps either to hold the tissues together and reduce the tension on the suture, or to spread the suture and/or tissues apart to increase the tension on the suture, thereby allowing the operator to precisely control the tension applied to the suture material. The forceps serve the additional purpose of keeping the suture elevated off of the tissues, to reduce any potential thermal injury which might occur during the shortening process. Both ends of the suture should be secure, as is the case when a suture is implanted into a warm blooded animal. If a small energy spot is used, such as that produced by a laser, the energy must be applied in a sweeping fashion along the length of the suture, usually at a faster rate than during shrinkage. During stretching, the use of slower rates such as those used during shrinking, frequently results in rapid thinning and breakage at the point of energy application.

Once energy is applied, the suture will show evidence of elongation and thinning. The rate of thinning is dependent on the same four factors used to determine axial shrinkage and cross-sectional enlargement; namely, (1) the density of the energy employed; (2) the length of time the energy is applied; (3) the amount of tension present in the suture; and (4) the maximum amount of stretch obtainable for the given material used. Typically, the suture will stretch at the point of energy application. As the energy is swept along the suture, further stretching will occur until the tension is relieved or the entire suture is treated. For instances where the amount of stretch is within the amount possible for the material used, this is an ideal property for the adjustment of a tight suture in vivo, as it will allow for only enough stretching to relieve the excess tension, resulting in a well tensioned suture.

Unlike shrinkage, the amount of stretch is not entirely predetermined by the manufacturing process. As additional energy is applied, stretching can usually be continued, making the suture thinner and thinner in cross-sectional area, until suture lysis occurs. However, in order to maintain reasonable tensile strength, only a controlled amount of stretching is feasible. This amount is largely controlled by the manufacturing process, and the surgeon must not exceed it.

The second factor which influences the type of changes which occur on the application of energy is the manufacturing process, and generally three types of sutures can be made. In the first method, the suture is manufactured to provide the greatest amount of shrinkage possible. This characteristic is imparted during manufacturing through the use of a high degree of stretching with rapid quenching. The use of this type of suture is ideal for vascular and bowel anastomoses, as previously described, as well as tissues which are edematous at the time of surgery, such as occurs after trauma or the injection of local anesthetic agents into the wound margin, in which the suture may slacken as the inflammation decreases post-operatively. In general, the amount of shrinkage imparted by this method is from about 5 to 80%, preferably from about 40 to 60%.

A second method of manufacturing involves the production of a material which can either be elongated or shortened through the application of energy. This characteristic is imparted by employing only a part of the total amount of stretch. The use of this type of suture is best suited for microsurgical procedures, or delicate skin closures, in which placement of the suture is difficult and there replacement may result in undesirable trauma and scar formation. Adjustment of improperly tensioned sutures can be performed at the time of surgery, without the need for replacement and further tissue trauma. An example of a microsurgical procedure for which this is well suited is cataract surgery. An improperly tensioned suture must currently be replaced, resulting in further damage to the delicate ocular tissues, and greater post-operative inflammation. Moreover, sutures that are well-tensioned at the time of surgery frequently result in undesirable astigmatic refractive errors astigmatic refractive errors in the post-operative period. Use of adjustable sutures in this setting would be preferred, as they would allow the surgeon the ability to precisely adjust the wound tension, and the resulting astigmatic refractive error both intra-operatively and post-operatively. In general, the amount of elongation imparted by this method is from about 5 to 40%, preferably from about 15 to 30%, and the amount of shortening imparted by this technique is from about 5 to 50%, preferably from about 20 to 40%.

In a third procedure, sutures can be manufactured to allow for the maximum amount of elongation. This is imparted during manufacturing by using the minimal amount of stretch necessary to impart sufficient orientation so as to provide adequate tensile strength to the suture material. Use of these sutures is ideally suited for tissues in which significant postoperative edema is expected, such as occurs after rotational skin flaps. In general, the amount of elongation imparted by this method is from about 5 to 60%, preferably from about 20 to 40%.

A heat-sensitive material for the apposition of tissues in accordance with the present invention must be non-toxic when placed in warm blooded animals, and generally should possess a melting point of from about 50° to 150° C., preferably from about 50° to 70° C., to minimize damage to biological tissues during energy application. The use of materials that form crosslinks between the long molecular chains in the polymer when irradiated, is preferred.

A number of energy sources can be used to apply energy to sutures. Energy sources in addition to heat include, but are not limited to, ultrasound, energy in the electromagnetic spectrum including monochromatic coherent light, monochromatic non-coherent light, polychromatic coherent light, polychromatic non-coherent light, electrical energy, in a continuous or non-continuous fashion. Energy from a hot air gun, warm water bath, or microwave can also be used. Most preferred are the use of lasers including, but not limited to THC:YAG, Nd:YAG, argon, krypton, carbon dioxide, diode, and the excimer laser.

The range of polymers useful for making sutures is enhanced by the addition of light absorbing substances (i.e. dyes and chromophores) to the polymer. For this purpose, broad band absorbers such as a black dye or selective absorbers for the particular laser may be employed. Preferably, the dye is chosen on the basis of its ability to absorb light energy at the wavelength of a specific laser light source. The choice of a laser whose light output is poorly absorbed by biologic tissue, but well absorbed by the dyed suture, would ensure minimum collateral damage to adjacent tissue. This would be the case even if the polymer required a temperature of shrinkage that was well above that which causes tissue necrosis.

Example of dye laser combinations, include, but are not limited to, fluorescein isothiocyanate (absorbance: 490 nm) and an argon laser operating at 488-514 nm; green compounds which absorb in the region of 808 nm such as indocyanine green (absorbance when dissolved in water: 770 nm) and a diode laser operating at 808 nm; various silver compounds including silver nitrate (broad absorbance) and a krypton laser (676 nm); dye compounds such as rose bengal, nile blue and Evans blue absorbing in the range of 200 to 610 nm, and corresponding dye lasers; and Q-Switched II TM (Eastman Kodak), which absorbs light from a Nd:YAG laser at 1064 nm, and 1320 nm. Sudan III, Sudan black B and India Ink may also be utilized to absorb light from any of the above mentioned lasers.

In particular, the combination of a dyed suture and diode laser may be employed. Delivery of the laser energy is preferably by means of a fiber optic cable. The energy density is generally between 1 and 40 Watts/cm$^2$, preferably 5 and 20 Watts/cm$^2$, delivered in a continuous manner.

EXAMPLE 1

3 strips of irradiated cross-linked polyethylene plastic (Frost King TM Shrink-Fit Window Insulation Kit manufactured by Thermwell Products Co., Paterson, N.J.) measuring 5.79±0.07 inches × 1.0 inch were rolled into a cylinder having a diameter of 3/16". The strips were placed into a gas oven and heated at 185° F. and for 12 minutes. The materials were removed from the oven allowed to cool and then measured. The results are shown in Table 1.

The three samples were then placed into the oven and heated to a temperature of 230° F. for 17 minutes. The samples were removed allowed to cool and then measured with the results shown in Table 1.

The three samples were again placed into the oven and heated at 300° F. for 10 minutes and measured in the same way as described above.

As shown in Table 1, the 3 strips showed a decrease in their length based on the amount of exposure to heat.

TABLE 1

| Pre-Heat | 185° F. | 230° F. | 300° F. |
|---|---|---|---|
| 5.79 ± 0.07 in. | 5.44 ± 0.06 in. | 4.79 ± 0.07 in. | 1.54 ± 0.09 in. |

As shown by the results in Table 1, the suture material can be shortened in a controlled amount by the amount of heat applied to the material.

COMPARATIVE EXAMPLE 1

3 6" strips of polypropylene 0 and 5-0 suture (Prolene ™ manufactured by Ethicon, a division of Johnson and Johnson) were treated and measured in the same manner as Example 1. The results are shown in Table 2.

TABLE 2

| SAMPLE | PRE-HEAT | 185° F. | 230° F. | 300° F. |
|---|---|---|---|---|
| Prolene 0 | 5.79 ± 0.07" | 5.75 ± 0" | 5.75 ± 0" | 5.66 ± 0.07" |
| Prolene 5 | 5.70 ± 0.07" | 5.75 ± 0" | 5.75 ± 0" | 5.66 ± 0.07" |

The results shown in Table 2 indicate that the comparative sutures do not change dimensions at low temperatures, and only show an insignificant reduction in length at temperatures which expose the surrounding tissues to possible damage.

EXAMPLE 2

An irradiated cross-linked polyolefin-containing thermoplastic (manufactured by SPC Technology, Chicago, Ill.), dyed black, was fashioned into thin strips, with a 1.0 mm² square cross-sectional area. The strips were then subjected to heated air of around 100° C., while gentle traction was applied. This resulted in a 25% increase in the length, a commensurate decrease in cross-sectional area, and a more circular cross-sectional profile. The resulting strips had a configuration, and handling characteristics similar to 0 sutures. The tensile strength before break was moderate as compared to 0 polypropylene sutures (Prolene ™, manufactured by Ethicon ™, a division of Johnson and Johnson).

The suture material was cut into 6" lengths. The suture was held in a loose fashion, similar to that seen postoperatively in the case of a loose skin suture. Laser energy was applied using a Coherent ™ 810 Diode Laser (Coherent, Inc., 3270 West Bayshore Road, P.O. Box 10122, Palo Alto, Calif. 94303) emitting 300 mW, for 1.0 second duration at a repetition rate of 0.2 seconds through an Acculite ™ Endoprobe Delivery System with a spot size of 2 mm, and an energy density of 10 Watt/cm².

The laser spot was applied in a sweeping fashion along the axis of the suture. The sweep speed was maintained at 1 cm per 5-10 seconds, to prevent suture melting and lysis and boiling of the suture material. When laser energy was applied and the suture was not held in place, a kink occurred at the point of laser energy application, preventing controlled shrinkage, and frequently leading to suture lysis.

On the application of the laser energy, the area around the spot showed evidence of contraction, and enlargement of its cross-sectional diameter. The amount of axial shrinkage and cross-sectional enlargement were controlled by four factors: (1) the density of the energy employed; (2) the length of time the energy is applied; (3) the amount of slack present in the suture; and (4) the maximum amount of shrinkage obtainable for the given material used. The maximum reduction in length possible for the sutures used in this example was 66%. The suture contracted an amount equal to the amount of slack present in the suture material, and then stopped. This is ideal for the adjustment of a loose suture in vivo, as it will allow for shortening of the suture until all the excess slack is removed, and will stop without the production of excess tension as can frequently occur after manual suture placement.

The amount of shrinkage obtained using the suture material described in this example, on exposure to the laser energy density as described above, is shown in Table 3.

TABLE 3

| START | 3 MINUTES | % SHRINKAGE |
|---|---|---|
| 6" | 2" | 66% |
| 6" | 2¼" | 63% |
| 6" | 2" | 66% |

As a control, a 6" strip of 0 polypropylene suture (Prolene ™, Ethicon) was dyed with black permanent marker (El Marko ™, Paper Mate). On heating the suture, the suture contracted at the site of laser application, and then formed a ball of plastic on either side of the spot. Overheating resulted in suture lysis (i.e. cutting). Shrinkage could not be achieved. It was found that the axial length of existing polypropylene suture cannot be adjusted through dye enhancement in combination with a diode laser in the fashion similar to that used for the suture described in the present invention.

EXAMPLE 3

The same suture material described in Example 2 was dyed black and fashioned into sutures in the same manner as in Example 2, except that the sutures were not elongated before laser treatment. The suture material was cut into 6" strips. The suture was held in a slightly taut fashion. Laser energy was applied using a Coherent 810 Diode Laser emitting 300 mW for 1.0 second duration at a repetition rate of 0.2 seconds through an Acculite ™ Endoprobe Delivery System with a spot size of 2 mm. The energy spot was applied in a similar fashion as was described in Example 3.

The laser spot was applied in a sweeping fashion along the length of the suture. The sweep speed was maintained at ½ to 1 cm per second, in order to prevent suture melting and lysis and boiling of the suture material. During stretching, the sweep rate of the laser was more important than during shrinking. During stretching, the use of slower rates such as those used during shrinkage, frequently resulted in rapid thinning and breakage at the point of energy application.

On the application of laser energy, the suture showed evidence of elongation and thinning. The maximum amount of stretch possible without resulting in more than a moderate reduction in length, was 30%. Additional stretching was possible, but generally resulted in an unacceptable reduction in tensile strength. Typically, on the application of energy in a sweeping fashion, the suture would stretch at the point of energy application. As the laser was swept along the suture, further stretching would occur until the tension was relieved or the entire suture was treated.

The amount of stretching obtainable using the suture material described in this example, on exposure to the laser energy density as described above, is shown in Table 4.

TABLE 4

| START | 5 MINUTES | % ELONGATION |
|---|---|---|
| 6" | 8¼" | 37.5" |
| 6" | 7½" | 25 |
| 6" | 8" | 33 |

EXAMPLE 4

The same suture material described in Example 3 was fashioned into sutures in the same manner as in Example 3. In Example 2, the sutures were elongated through the application of laser energy. In this example, the same sutures were shortened. The suture material was cut into 6" strips. The suture was held in a loose fashion. Laser energy was applied using a Coherent TM 810 Diode Laser emitting 300 mW for 1.0 second duration at a repetition rate of 0.2 seconds through an Acculite TM Endeoprobe Delivery System with a spot size of 2 mm, and an energy density of 10 Watts/cm$^2$.

The laser spot was applied in a sweeping fashion along the length of the suture. The sweep speed was maintained at 1 cm per 5-10 seconds.

On the application of the laser energy, the area around the spot showed evidence of contraction and enlargement of the diameter.

The amount of shrinkage obtained using the suture material described in this example, on exposure to the laser energy density as described above, is shown in Table 5.

TABLE 5

| START | 3 MINUTES | % SHRINKAGE |
|---|---|---|
| 6" | 3" | 50% |
| 6" | 3¼" | 46% |
| 6" | 3" | 50" |

This example demonstrates that sutures can be manufactured in a fashion which allows them to either be elongated or shortened, depending on the desired application. Elongation is accomplished by heating the suture when it is under tension. Shortening is accomplished by heating the suture when the suture is loose.

EXAMPLE 5

The same suture material as described in Example 2 was treated in the same manner as in Example 2. A 1.5 cm incision was made in freshly harvested rat skin (Bioproducts for Science, Inc. Indianapolis, Ind.). Water was injected into the tissue adjacent to the incision using a 25 G needle to simulate edema. The incision was closed with three sutures, in a well tensioned fashion. The skin around the suture site was then pressed between an absorbable material until the injected fluid was extracted, thereby resolving the "tissue edema". The distance between insertion points of the suture into the skin were measured as was the total length of the suture. The amount of "loose" or "excess" suture was determined by subtracting the distance between the suture insertion points from the total length of the suture. Diode laser energy (810 nm) was applied in a similar fashion as described in Example 2, until there was no excess suture, and it was well tensioned. Suture strength was then grossly tested by pulling on the two ends of the wound with forceps, and was found to be similar to the preshrunk strength. The results are shown in Table 6.

TABLE 6

| TOTAL LENGTH (MM) (=2 × LOOP LENGTH) | DISTANCE BETWEEN INSERTION POINTS | EXCESS SUTURE (MM) C-COLUMN A- COLUMN B | % SHRINKAGE |
|---|---|---|---|
| 10 | 6 | 4 | 40% |
| 12 | 8 | 4 | 33% |
| 12 | 8 | 4 | 33% |

On visual examination, there was little evidence of collateral thermal injury or charring of the tissues after the laser adjustment of the sutures.

EXAMPLE 6

The same suture material as described in Example 2 was fashioned into sutures in the same manner as in Example 3. A 2.0 cm incision was made in freshly harvested rat skin (Bioproducts for Science, Inc. Indianapolis, Ind.). The incision was closed with three sutures, in a well tensioned fashion. The suture length was then measured. An injection of water was made into the tissue surrounding using a 25G needle to simulate tissue edema as can occur post-operatively, making the sutures taut. The bent tips of a pair of forceps were inserted under the suture, and spread using a moderate amount of force. This served to provide control during stretching, and also elevated the suture off the skin surface to prevent collateral thermal injury to the tissues. Diode laser energy (810nm) was applied in a similar fashion as described in Example 2, until the tension on the suture created by the "tissue edema" was relieved.

The skin around the suture site was pressed between an absorbable material until the injected fluid was extracted, thereby resolving the "tissue edema". The length of the suture loop was measured. The amount the suture had been elongated was determined by subtracting the original length from the suture length after "resolution" of the tissue edema. The results are shown in Table 7.

TABLE 7

| ORIGINAL LENGTH (MM) (=2 × LOOP LENGTH) | FINAL LENGTH (MM) | ELONGATION (MM) C-COLUMN A-COLUMN B | PERCENTAGE ELONGATION |
|---|---|---|---|
| 8 | 10 | 2 | 25% |
| 10 | 14 | 4 | 40% |
| 8 | 10 | 2 | 25% |

On visual examination, there was no evidence of collateral thermal injury or charring of the tissues as a result of the laser adjustment of the sutures.

EXAMPLE 7

A sheet composed of a combination of polyethylene and polyvinyl acetate (3M Window Insulator Kit, Household Products Division/3M Company, St. Paul, Minn. 55133) were cut into approximately 1 mm wide strips, with a thickness of less than 0.1 mm, and a length of 6". A black permanent marker (El Marko TM, Paper Mate) was used to dye one side of the plastic, resulting in black 6" model sutures. Although similar in width to 0 sutures, these model sutures were much thinner and showed only minimal tensile strength, as compared to 0 polypropylene suture (Prolene TM, Ethicon TM).

The suture was held in a loose fashion, similar to that used in Example 2. Diode laser energy was applied in a similar manner to Example 2, except that the sweep speed was increased to 2–5 seconds per cm.

On the application of the laser energy, the area around the spot showed evidence of contraction. The amount of shrinkage was controlled by the same factors as described in Example 2. The maximum reduction in length possible for the sutures used in this example was 66%.

The amount of shrinkage obtained using the suture material described in this example, on exposure to the laser energy density as described above, is shown in Table 8.

TABLE 8

| START | 3 MINUTES | % SHRINKAGE |
|---|---|---|
| 6" | 2¾" | 54% |
| 6" | 2¾" | 54% |
| 6" | 2¼" | 63% |

EXAMPLE 8

Polyvinyl chloride (PVC), (Scotchtite TM 105° C., 3M Company) was used to fashion sutures into strips which were approximately 0.7 mm wide and 0.4 mm thick. These sutures were cut into 6" strips. These sutures were similar to 0 sutures, except that they were rectangular in cross-sectional area.

The suture was held in a loose fashion, similar to that used in Example 2. Diode laser energy was applied in a similar manner to Example 2, except that the sweep speed was decreased to 10–15 seconds per cm.

On the application of the laser energy, the area around the spot showed evidence of contraction and visibly swelled in diameter. The amount of shrinkage was controlled by the same factors as described in Example 2. The maximum reduction in length possible for the sutures used in this example was 50%.

The amount of shrinkage obtained using the suture material described in this example, on exposure to the laser energy density as described above, is shown in Table 9.

TABLE 9

| START | 3 MINUTES | % SHRINKAGE |
|---|---|---|
| 6" | 4¼" | 29% |
| 6" | 4¼" | 29% |
| 6" | 4⅜" | 27% |

EXAMPLE 9

A sheet composed of polypropylene (Insulating Shrink-Film, Manco, Inc., 830 Centerbury Road, Westlake, Ohio) were prepared and treated in the same manner as Example 7. The results are shown in Table 10.

TABLE 10

| LENGTH | AFTER LASER | % SHRINKAGE |
|---|---|---|
| 6" | 3¼ | 46% |
| 6" | 3⅜ | 44% |
| 6" | 3 | 50% |

What we claim is:

1. A method of treating tissues and prosthetic materials, comprising:
    (a) suturing the tissue or prosthetic material with a flexible heat-sensitive polymeric material adapted to undergo a change in dimension in vivo upon the application of energy to the flexible material; and
    (b) applying energy to the flexible material effective to cause said in vivo change in dimension.

2. The method of claim 1 wherein the heat-sensitive polymer is cross-linked.

3. The method of claim 1 wherein the heat-sensitive polymers are selected from the group consisting of silicone rubber, polystyrene, substituted and unsubstituted polyolefins, poly(vinylidene chloride), polyesters, poly(vinyl chloride), poly(vinyl fluoride), coated cellophanes, poly(vinyl acetate), poly(methyl methacrylate), or combinations thereof.

4. The method of claim 3 wherein the heat-sensitive polymers is a polyolefin, a mixture of polyolefins, or a mixture of polyolefins and at least one other of said heat-sensitive polymers.

5. The method of claim 1, wherein said energy is applied to effect a lengthening of said flexible material in vivo.

6. The method of claim 1, wherein said energy is applied to effect a shortening of said flexible material in vivo.

7. The method of claim 1 wherein the flexible material comprises an energy absorbing compound, said process comprising applying laser energy to said flexible material at a wavelength which is absorbed by said energy absorbing compound to thereby change the dimension of the flexible material.

* * * * *